(12) United States Patent
Klyosov et al.

(10) Patent No.: US 6,642,205 B2
(45) Date of Patent: Nov. 4, 2003

(54) METHODS AND COMPOSITIONS FOR REDUCING SIDE EFFECTS IN CHEMOTHERAPEUTIC TREATMENTS

(75) Inventors: Anatole Klyosov, Newton, MA (US); David Platt, Newton, MA (US)

(73) Assignee: Pro-Pharmaceuticals, Inc., Newton, MA (US)

(*) Notice: Subject to any disclaimer, the term of this patent is extended or adjusted under 35 U.S.C. 154(b) by 0 days.

(21) Appl. No.: 09/961,681

(22) Filed: Sep. 24, 2001

(65) Prior Publication Data

US 2002/0068077 A1 Jun. 6, 2002

Related U.S. Application Data (60) Provisional application No. 60/235,141, filed on Sep. 25, 2000.

(51) Int. Cl.[7] ........................ A61K 9/127; A61K 31/70; C07H 1/00
(52) U.S. Cl. ........................ 514/34; 514/42; 514/432; 514/12; 514/8; 514/24; 536/123.1; 536/1.11
(58) Field of Search ................. 514/34, 24, 42, 514/432, 12, 8; 424/450; 536/123.1, 1.11

(56) References Cited

U.S. PATENT DOCUMENTS 5,955,100 A * 9/1999 Bosslet et al.

FOREIGN PATENT DOCUMENTS

WO    WO 96/19243    6/1996

OTHER PUBLICATIONS

Palomino E: "Carbohydrate Handles as Natural Resources in Drug Delivery", Advanced Drug Delivery Reviews, Amsterdam, NL. vol. 13, 1994, pp. 311–323, XP000775555 Issn: 0169–409X, p. 317, paragraph 4, p. 320, paragraph 3.

European Search Report.

* cited by examiner

*Primary Examiner*—Jose' G. Dees
*Assistant Examiner*—Robert M DeWitty
(74) *Attorney, Agent, or Firm*—Bromberg & Sunstein LLP (57) ABSTRACT

A pharmaceutical compound and a process for making the compound is provided where the compound includes a therapeutic agent, a spacer and a galactose, the spacer being covalently linked to the therapeutic agent at a first site on the spacer and covalently linked to the galactose by an ether bond at a second site on the spacer to form a conjugate. The conjugate may be used to treat a subject suffering from a medical condition, so as to reduce the side effects associated with the therapeutic agent by administering an effective dose of the conjugate to the subject so that the side effects in the subject are less then they would have been with the unconjugated therapeutic agent.

29 Claims, 2 Drawing Sheets

METHODS AND COMPOSITIONS FOR REDUCING SIDE EFFECTS IN CHEMOTHERAPEUTIC TREATMENTS

CROSS REFERENCE TO RELATED APPLICATIONS

This application gains priority from provisional patent application Ser. No. 60/235,141 filed Sep. 25, 2000, the provisional application being herein incorporated by reference.

TECHNICAL FIELD AND BACKGROUND ART

The present invention relates to reducing side effects of therapeutic agents in a subject without substantial loss in efficacy where the agents would otherwise have significant side effects. This beneficial effect is achieved by coupling a galactose residue to the agent via a spacer.

Directed delivery of an agent to a target site is desirable to minimize side effects in patients and to enhance therapeutic efficacy. Side effects are the hallmark of many chemotherapeutic agents which otherwise are effective in reducing tumor size. For example, anthracycline antibiotics such as Adriamycin (also called 14-hydroxydaunamycin or doxirubicin) are effective anti-tumor agents. (Arcamone, "Doxorubicin: Anti-Cancer Antibiotics", Medicinal Chemistry Series, (1981) Vol. 17, Academic Press; C. R. Hutchinson, "The Biosynthesis of Tetracycline and Anthracycline Antibiotics," in Antibiotics IV Biosynthesis, (1981) pp. 1–11, Ed.: J. W. Corcoran, Pub.: Springer-Verlag; R. J. White, "Anthracyclines," in Biochemistry and Genetic Regulation of Commercially Important Antibiotics, (1983) p. 277–291, Ed.: L. C. Vining, Pub.: Addison Wesley).

In addition to the desired effect of destroying cancer cells, anthracycline antibiotics also damage non-cancer cells resulting in side effects for the patient. These side effects limit the dose and duration of treatment with these agents. Attempts have been made to reduce the side effects of this class of therapeutic agent. In U.S. Pat. No. 5,814,608, the daunosamine moiety of the Adriamycin was substituted with several disaccharide moieties and the modified agent tested using human tumor cell lines showing a marked reduction in cytotoxic potency for the target tumor cells (Arcamone, 1981). These in vitro assays did not however measure side effects which arise in a patient nor indeed did they provide information on cytotoxic effects on non-target cells. An analog of doxorubicin has been made in which a disaccharide replaces the monosaccharide daunosamine of doxorubicin. These compounds actually had increased side effects (Zunino et al., Biochemical Pharmacology (2001) Vol. 61, pp. 933–938; Gonzalez-Paz et al. European Journal of Cancer (2001) Vol. 37, pp. 431–437). It was shown that natural mono-, di- and tri-saccharide derivatives of pyrromycinone possess a progressively increased DNA binding activity with the increase in the length of the oligosaccharide chain. (DuVernay V. H., "Molecular Pharmacology of Anthracycline Antitumor Antibiotics", in Canver and Chemotherapy, (1981) Vol. III, pp. 233–271, Academic Press, New York.) Although an increase in DNA binding activity was shown, this does not actually mean anti-tumor potency.

Other approaches to reducing side effects have been developed which rely on directing therapeutic agents in the form of pro-drugs to their target site of action. Pro-drugs of Adriamycin were made in which the Adriamycin was linked to spacers at C14, which in turn were linked to ligands, the ligands including monosaccharides. The pro-drugs were then linked to antibodies which directed the pro-drug to target cells. The pro-drugs were hydrolyzed by enzymes which were co-administered with the pro-drugs. The intended result was liberation of the active agent at the target site only. (Leenders et al., Tetrahedron Letters (1995) Vol. 36, pp. 1701–1704; Ghosh et al., Tetrahedron Letters (2000) Vol. 41, pp. 4871–4874; Houba et al., International Journal of Cancer, (2001) Vol. 91, pp. 550–554). In vivo data suggested that pro-drugs were much less toxic compared to the parent agent (Adriamycin) and showed a somewhat higher tumor growth inhibition compared to the parent agent.

SUMMARY OF THE INVENTION

In a first embodiment of the invention there is provided a pharmaceutical compound, that includes a therapeutic agent, a spacer and a galactose, the spacer being covalently linked to the therapeutic agent at a first site on the spacer and covalently linked, at a second site, to at least one galactose by an ether linkage. In examples of the embodiments, the spacer may be polyhydroxylated. The spacer may be an aldose or a ketose, and may further be a triose, tetrose, pentose, hexose or septose. The spacer may be have the chemical composition:

where n = ≥ 0 and <20 or where n=≧0 and <20 and m=≧0 and <20. The presence of the spacer between a therapeutic agent and a galactose causes the galactose to be separated from the therapeutic agent by at least two carbon atoms. The covalent linkage between the spacer and the agent is formed with a reactive group on the therapeutic agent, the reactive group being selected from an amino group, an alkoxy group, a hydroxy group, a carbonyl group, a carboxylic group, a halogen and a thiol group.

In an embodiment of the invention, the therapeutic agent is Adriamycin which is covalently linked to an amide group on the daunosamine via for example an aldose or ketose spacer. In particular embodiments of the invention, the galactose is linked to the spacer by means of a glycosidic linkage. For example, the pharmaceutical compound may include N-[β-D-galactopyranosyl-(1→4)-β-O-D-sorbityl] doxorubicin or N-[α-D-galactopyranosyl (1→6) 6β-O-D-sorbityl]doxorubicin.

In an embodiment of the invention, a pharmaceutical preparation, is provided that includes an effective dose of any of the pharmaceutical compounds described above and a pharmaceutically acceptable excipient.

In another embodiment of the invention, a method is provided for synthesizing a pharmaceutical compound that includes: providing (i) a therapeutic agent; and (ii) a spacer linked to a galactose conjugate; protecting reactive groups on the therapeutic agent other than the reactive site for linking to the spacer; reacting the protected therapeutic agent with the spacer linked to the galactose; and deprotecting the therapeutic agent to form the pharmaceutical compound. For example, the spacer linked to galactose has a formula:

where n=≧0 and ≦20 or where n=≧0 and ≦20 and m=≧0 and <20.

In another embodiment of the invention, a method is provided for treating a subject suffering from a medical condition, so as to reduce the side effects associated with a therapeutic agent selected for treating the condition, without substantially reducing efficacy, comprising: providing as a conjugate, the therapeutic agent covalently linked to a spacer at a first site and the spacer being covalently linked to galactose at a second site; and administering an effective dose of the conjugate to the subject so that the side effects in the subject are less then they would have been with the unconjugated therapeutic agent.

According to the above, the medical condition may include any of a proliferative condition, high cholesterol, depression, asthma, hypertension and bacterial infections. If the condition is a proliferative condition, it may include cancers such as solid tumors, an invasive tumor such as occurs in brain tumors or circulating cancer cells such as occurs in leukemia. An example of a chemotherapeutic agent is Adriamycin the conjugate corresponding to for example, N-[β-D-galactopyranosyl-(1→4)-β-O-D-sorbityl] doxorubicin and N-[α-D-galactopyranosyl-(1→6)-β-O-D-sorbityl]doxorubicin.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

Therapeutic agents that can be modified by a spacer linked to at least one galactose described in embodiments of the invention include any therapeutically active organic molecule that has a reactive group suitable for covalent attachment to the spacer so as to reduce unwanted side effects of the parent compound.

Formula 1

Galactose is a monosaccharide that belongs to the class of molecules identified as carbohydrates. Carbohydrates are attached to proteins and lipids to form glycoproteins and glycolipids. The carbohydrates play a myriad of critical roles in human metabolism. They facilitate cell adhesion and migration, and thereby help mediate the process of development. Carbohydrates aid protein function by ensuring correct protein folding, providing solubility and protease resistance, and targeting molecules both within cells and to specific cell types. Their roles in host defense include cell recognition and antigenicity.

Galactose is a hexose. It is a constituent of lactose, of plant polysaccharides (galactans) and of complex carbohydrates, such as glycoproteins, glycolipids and glycosaminoglycans. As such, galactose is involved in many functions in an organism. Galactose affects transcription in both prokaryotes and eukaryotes. For example, yeast cells react to the presence of galactose by expressing genes necessary to utilize the sugar as a source of energy. Galactose is also implicated in transcriptional regulation in multicellular eukaryotic organisms. For example, Zinc finger activators regulate expression of genes that are induced by galactose.

We have found that when one or more galactose moieties are attached to a therapeutic agent via a spacer, side effects normally associated with the agent are reduced when the compound is administered to a subject. The spacer provides a bridge between the therapeutic agent and the galactose which facilitates orientation of the galactose with respect to the agent and is a means to avoid inappropriate interactions between the agent and galactose. Accordingly, the spacer includes 2 or more carbons in a core structure. The reactive sites with which to link the spacer to the agent and to link the spacer to galactose can be at distant ends of the spacer or may be internal to the core structure. Indeed, the spacer may have multiple reactive sites so as to facilitate the linkage of more than one galactose to the spacer in addition to the therapeutic agent. In the latter case, the galactose and the agent should nonetheless be separated on the spacer so as to avoid steric hindrance. The spacer may be polyhydroxylated although non-polyhydroxylated spacers may be used providing the reactive sites are available to enable the spacer to serve as a bridge between the therapeutic agent and galactose. In addition to the linkage groups, the spacer may further include a variety of side groups that do not interfere with the spacer function as described above.

The spacer be linked to the galactose by any appropriate means that would be recognized by one of skill in the art. For example, galactose may be linked to the spacer by means of a condensation reaction between any hydroxyl group on the galactose and a hydroxyl group on the spacer to form an ether linkage.

Figure 1:
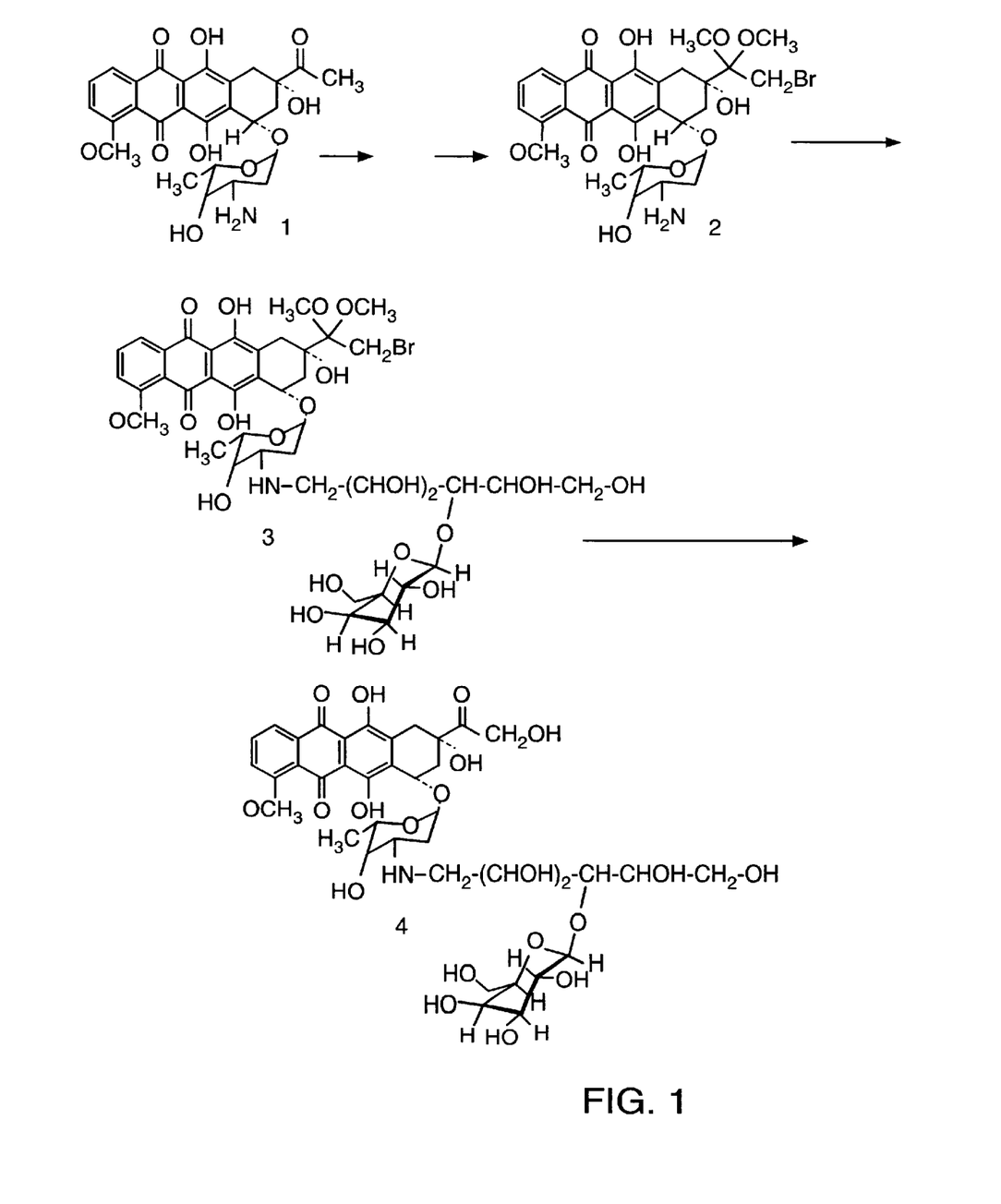
FIG. 1 is a synthetic pathway for N-[β-D-galactopyranosyl-(1→4)-β-O-D-sorbityl]doxorubicin
Figure 2:
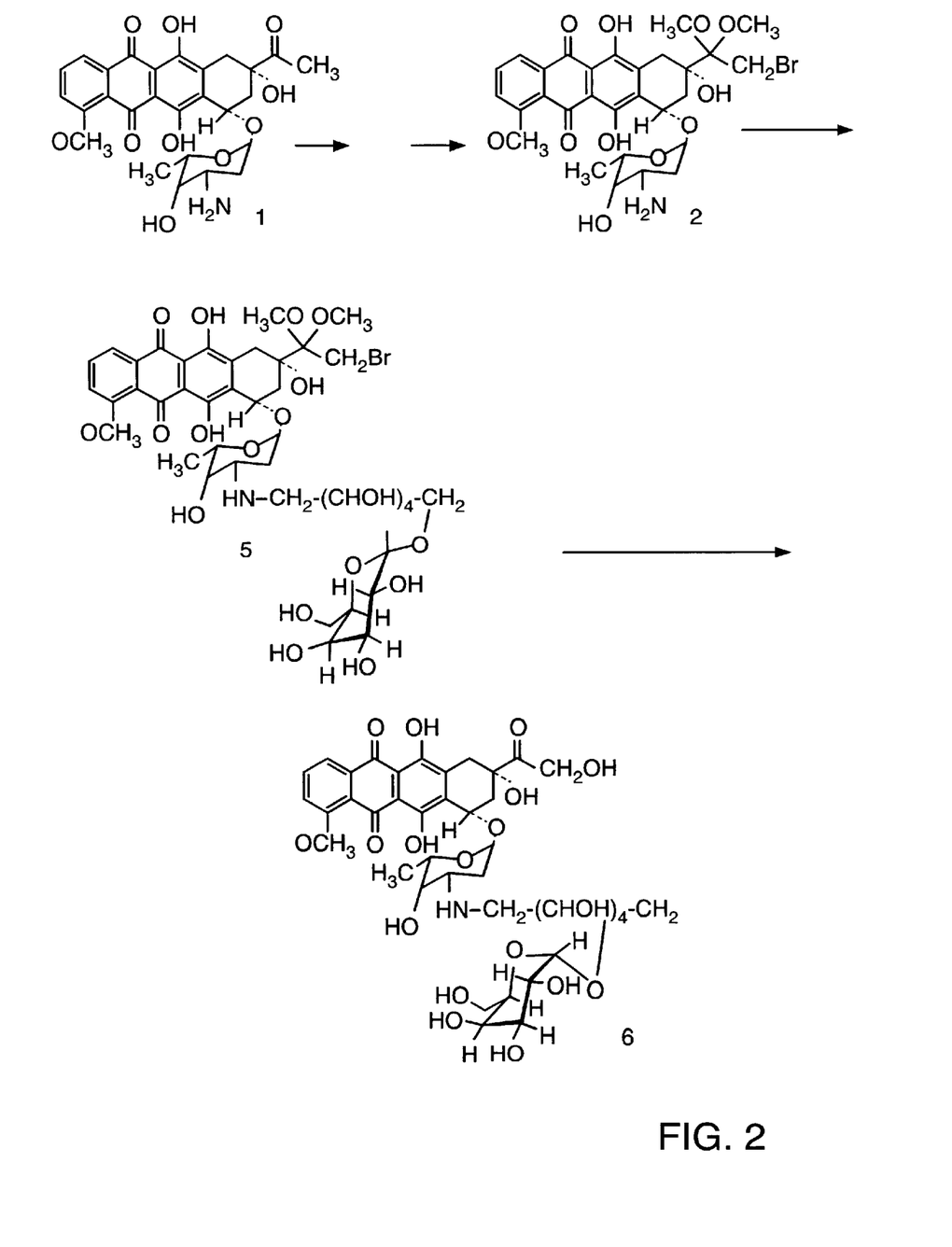
FIG. 2 is a synthetic pathway for N-[α-D-galactopyranosyl-(1→6)-β-O-D-sorbityl]doxorubicin.

The spacer may be linked to the therapeutic agent by any appropriate means that would be recognized by one of skill in the art. (See for example Vladimir Torchilin "Immobilized Enzymes in Medicine" Ser. Progress in Clinical Biochemistry and Medicine (1991) Vol. 11, pp. 206, Pub.: Springer Verlag, New York, which is herein incorporated by reference). A suitable site for linking a spacer to a therapeutic agent would be through a reactive group on the agent such as for example a hydroxyl, alkoxyl, carboxylic, carbonyl, thiol, amine, halogen such as bromine, chlorine or fluorine, a sulfate or a nitrogen oxide. For example, in FIG. 1, the spacer has been linked to the therapeutic agent through an amine group on the daunosamine of Adriamycin. Examples of therapeutic agents with reactive groups as described above include: Omeprazole, Simvastatin, cytosine arabinoside, cyclophosphamide (Cytoxan), melpalan (Alkeran), chlorambucil (Leukeran), idarubicin, itoxantrone, methotrexate, 6-thioguanine, 5-fluorouracil (5-FU), cytosine arabinoside (Ara C, cytosar), L-asparaginase (Elspar), dacarbazine (DTIC), hydroxyurea (Hydrea), procarbazine (Matuline), Acetimophen, Paclitaxel, Atorvastatin, Fluoxetine, Sertraline, Albuterol, Amlodipine, Amoxicillin, Lisinophril, Clarithromycine, Cetirizine, Prevastatin, Cephalexin, Warfarin, Enalapril, Atenolol, Furosemide, Levothyroxine, Ciprofloxacin, Prednisone and Adriamycin.

A function of the spacer is to place the therapeutic agent in a suitable orientation with respect to galactose. A wide range of spacers have been described in the prior art that are designed to achieve this function and may be applicable here. (Torchilin (1991)). In an embodiment of the invention, a novel spacer in the form of an open saccharide such as an aldose or a ketose has been found to be effective with respect to galactose and a therapeutic agent.

The composition of the spacer may be as follows:

or where $n=\geq 0$ and $<20$ and $m=\geq 0$ and $<20$.

The galactose may be linked via an ether bond to the spacer with the galactose being in either a D form or L form. If the spacer is linked to the anomeric carbon of galactose, the linkage may be via a glycosidic bond.

In embodiments of the invention, chemotherapeutic agents which are coupled to a spacer and galactose to reduce side effects without substantially reducing efficacy can be used to treat a wide range of cancers that affect any of the tissues in the body including colon, ovary, breast, lung, pancreas, prostate, and uterus. It is envisaged that reduction in side effects of agents other than chemotherapeutic agents can be achieved through linkage of a spacer-galactose to, for example, anti-inflammatory agents, anti-psychotic agents, anti-infective agents, anti-depressants, weight reduction agents, anti-hyperlipidemic agents and anti-ulcerative agents.

"Anthracycline antibiotics" are therapeutic compounds that are widely used to treat tumors. They have a core structure consisting of an anthracycline with an attached sugar moiety on the seventh carbon, as illustrated below. Included in this definition are pharmaceutical salts as well as modifications and derivatives of the core structure such as for example, where the anthracycline is modified at the hydroxyl group on C14.

Anthracyclines with attached sugar moieties interfere with a nuclear enzyme, DNA topoisomerase II, which regulates replication, transcription and recombination of DNA. A widely used example of this class of agents is Adriamycin (14-hydroxydaunomycin, or doxirubicin) and Daunomycin. Adriamycin (doxorubicin) is a natural product, isolated from cultures of Streptomyces peutius var. caesius (U.S. Pat. No. 3,590,028). It has been synthesized from Daunomycin (J. Med. Chem., (1974) Vol. 17, pp. 659) and from 7-deoxydaunomycinone (U.S. Pat. No. 4,012,448). Anthracycline antibiotics cause severe side effects in a significant fraction of patients. For example, Adriamycin is cardiotoxic, having an $LD_{50}$ in mice of 21.1 mg/kg (Merck Index, (1996) 12th Ed.).

Compounds of Formula 1 described herein may contain one or more asymmetric centers and can thus occur as racemates and racemic mixtures, single enantiomers, diasteromeric mixtures and individual diasteromers. Embodiments of the invention are meant to comprehend all such isomeric forms of the compounds of Formula 1. Individual tautomers as well as mixtures thereof are encompassed by compounds of Formula 1 described herein.

"Halogen" includes fluorine, chlorine, bromine and iodine.

"Subject" refers to a living animal such as a mammal including dogs, cats, pigs, cows, sheep, goats, horses, rats, and mice. The subject may be a human in need of therapy for, or susceptible to, a condition or its sequelae. An individual that is normal in all respects is not intended to be excluded in this definition.

"Proliferative disease" includes cancer, especially a tumor disease including colon, ovary, breast, lung, pancreas and uterus or leukemia; and a non-malignant proliferative disease for example, atherosclerosis, thrombosis, psoriasis, scleroderma or fibrosis.

"Patient" shall mean a human subject who has presented at a clinical setting with a particular symptom or symptoms suggesting the need for treatment.

"Saccharide" refers to any of a monosaccharide, a disaccharide, an oligosaccharide and a polysaccharide and includes substituted forms of the same.

Dosage regimens are adjusted to provide the optimum desired response, e.g., a therapeutic response. The magnitude of prophylactic or therapeutic dose of the compound of Formula 1 will, of course, vary with the nature of the severity of the condition to be treated and with the particular compound and its route of administration. It will also vary according to the age, weight and response of the individual patient.

In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

A physician of ordinary skill in the art may determine and prescribe the effective amount of the therapeutic agent required. In general, a suitable daily dose of a compound of Formula 1 will be that amount which is the lowest dose effective to produce a therapeutic effect.

Another embodiment of the present invention provides compounds of Formula 1 and a pharmaceutically acceptable carrier. The term "preparation", as in pharmaceutical preparation, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

Accordingly, the pharmaceutical compounds of embodiments of the invention encompass any composition made by admixing a therapeutic agent conjugate, additional active ingredient(s), and pharmaceutically acceptable excipients. "Pharmaceutically acceptable carrier" includes any and all solvents, dispersion media, e.g., human albumin or cross-linked gelatin polypeptides, coatings, antibacterial and antifungal agents, isotonic, e.g., sodium chloride or sodium glutamate, and absorption delaying agents, and the like that are physiologically compatible. The use of such media and agents for pharmaceutically active substances is well known in the art.

Any suitable route of administration may be employed for providing a mammal, especially a human with an effective dosage of a compound of the present invention. For example, oral, rectal, topical, parenteral (including subcutaneous, intramuscular, and intravenous), by passage through mucosal membranes or by transdermal administration, or ocular (ophthalmic), pulmonary (aerosol inhalation), or nasal administration, can be employed. The active compound may be delivered by continuous infusion either from an external source or from a source of the compound placed within the body.

Dosage forms include tablets, troches, dispersions, suspensions, solutions, capsules, creams, ointments and aerosols. The most suitable route in any given case will depend on the nature and severity of the conditions being treated and on the nature of the active ingredient. They may be conveniently presented in unit dosage form and prepared by any of the methods well-known in the art of pharmacy.

Dosage forms suitable for oral administration may comprise tablets, pills, capsule, multiparticulates including: granules, beads, pellets and micro-encapsulated particles; powders, elexirs, syrups, solutions and aqueous or oily suspensions. For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos.: 3,845,770; 3,916,899; 3,536,809; 3,598,123; 3,630,200 and 4,008,719.

"Efficacy" of a therapeutic agent refers to the relationship between a minimum effective dose and an extent of side effects. Efficacy of an agent is increased if a therapeutic end point can be achieved by administration of a lower dose or a shorter dosage regimen. If side effects can be decreased, a therapeutic agent can be administered on a longer dosage regimen or even chronically with greater patient compliance and improved quality of life. Further, decreased side effects of an agent enables the practitioner to increase the dosage to achieve the therapeutic endpoint sooner, or to achieve a higher therapeutic endpoint.

"Side effects" are undesirable or adverse and are associated with non-target tissue in a subject that sustains some change that is a byproduct of treatment of the target. Side effects include cytotoxicity for non-target cells and undesirable functional changes in the subject.

"Nonspecific death" is death of a treated tumor-bearing animal if its day of death was statistically less ($P \leq 0.05$) than the corresponding day of death of a tumor-bearing animal in the untreated control group.

We have exemplified embodiments of the invention by demonstrating the two different chemical syntheses used to create a therapeutic agent linked to a bifunctional spacer linked in turn to galactose.

To illustrate a general scheme of synthesis for a therapeutic agent linked to galactose via a bifunctional spacer we synthesized 14-bromodaunorubicin dimethylketal (2), obtained from Adriamycin (1) according to Povarov et al., Zh. Org. Khim., 1979, (Moscow) Vol. 15, pp.1560–1561; Olsufieva et al., Bioorgan. Khim., 1990, (Moscow) Vol. 16, pp. 856–862. The interaction of (2) with a galactose-containing disaccharide gave an Adriamycin derivative containing at the nitrogen atom of the daunosamine moiety a polyhydroxylated spacer connected with the galactose moiety via a derivative of 14-bromodaunorubicin dimethylketal. Starting from (2) and lactose (4-β-D-galactopyranosyl-D-glucopyranose) by the method of reductive alkylation with NaBCNH$_3$, N-[β-D-galactopyranosyl β4-O-D-sorbityl] doxorubicin (4) was obtained in 8% yield, after the hydrolysis of the intermediate bromoketal (3).

Similarly starting from (2) and melibiose (6-β-D-galactopyranosyl-D-glucopyranose), N-[α-D-galactopyranosyl β6-O-D-sorbityl]doxorubicin (6) was synthesized in 20% yield. Both compounds (4) and (6) contain a D-galactopyranose moiety connected with the antibiotic through a hydrophilic spacer. In compound (4) D-galactose has the β-anomeric configuration, while compound (6) has the α-configuration. In compound (4) the polyhydroxylated spacer is shorter (4 carbons) and more branched compared to compound (6) (6 carbons).

TLC and HPLC analyses show that compounds (4) and (6) contain no impurities of daunorubicin or Adriamycin. When hydrolyzed with 1N HCl (105° C., 1 hour), both (4) and (6) produce adriamycinone (the aglycone) and galactose (sorbitol and daunosamine were not analyzed), as demonstrated by paper chromatography using pure adriamycinone and galactose as standards. The structures of (4) and (6) were confirmed using $^{13}$C-NMR.

We have exemplified embodiments of the invention by demonstrating that when Adriamycin is modified by the addition of spacers linked to galactose, side effects are reduced as determined by reduction in non-specific death of mice while the efficacy of the agent measured in tumor bearing animals remains at least as good as the unmodified Adriamycin. (Examples 3 and 4).

EXAMPLES

Example 1

Synthesis of Galactomycin I, Conjugate (6) of Doxorubicin and Melibiose

To 1.3 g (2 mMol) of daunorubicin (1) in 20 mL MeOH, 10 mL dioxane, and 10 mL ethylorthoformate, 0.1 mL of $Br_2$ was added, and the reaction mixture was stirred for one hour at 23° C. Then 0.44 g of dry $K_2CO_3$ were added under stirring. The precipitate was filtered off quickly, and the filtrate was evaporated in vacuum at 35° C. The resulting crude 13-dimethylkethal-14-bromodaunorubicin (~1.5 g) (2) was dissolved in 65 mL of methanol, and 3.4 g (10 mMol) of melibiose in 30 mL of water was added. The reaction mixture was kept at 40° C. for four hours, then 0.275 g (4 mMol) of $NaCNBH_3$ in 0.5 mL of methanol was added, and the mixture was stirred overnight at 37° C. After that 0.275 g (4 mMol) of $NaCNBH_3$ in 0.5 mL of methanol was added, and the mixture was stirred at 37° C. for 24 hours. This procedure was repeated twice (totally 1.1 g, or 16 mMol of $NaCNBH_3$ were added) using TLC control on silica gel (Merck 60 F254:20×20 cm) in chloroform-methanol-water-formic acid (13:6:1:0.05). The resulting conjugate 5 had $R_f=0.50$, while the starting (2) showed $R_f=0.90$ in the same TLC system.

200 mL of water was added to the reaction mixture at room temperature, and the aqueous solution was extracted with chloroform (70 mL×3). The organic layers were combined, and extracted with aqueous 0.25 N HBr (50 mL×2). The dark red residue which precipitated between the layers was dissolved in 200 mL of aqueous 0.25 NHBr-methanol (1:1) mixture, and combined with the extracts of the red compound in aqueous 0.25 N HBr. The combined acidic aqueous extracts were incubated for 6 hours at 37° C., then 1.5 g of HCOONa in 1 mL of water (pH~4.5) was added, in order to hydrolyze 14-Br group. The reaction mixture was kept at 37° C. for 24 hours under TLC control in the chloroform-methanol-water-formic acid (13:6:1:0.05).

The resulting crude solution was the conjugate of doxorubicine with melibiose (6) ($R_f=0.28$). It was diluted with water to 500 mL, combined with approximately 100 mL of sorbent XAD-2, and stirred at room temperature for six hours until the red color of the solution disappeared. The red-colored sorbent was filtered off, washed with 500 mL of water, and compound (6) was eluted from it with the mixture of n-butanol-acetone-$H_2O$ (13:6:1). The eluate was evaporated, the dry residue was applied onto a column with silica gel Merck 60 (0.040–0.063), and eluted with chloroform-methanol-water-formic acid (13:6:1:0.05). The resulting fractions, containing compound (6), were combined and evaporated in vacuum to a small volume. Pure (6) (Galactomycin I) was precipitated with isopropanol, giving 390 mg (yield of 20%, starting from daunorubicin 1) of amorphous dark red powder, with m.p. 121–123° C. (decomp.)

Example 2

Synthesis of Galactomycin II, Conjugate (4) of Doxorubicin and Lactose

Compound 4 was obtained by a similar procedure as described above, starting from 1.3 g daunorubicin (1) and lactose. Amount of 4 bromohydrate obtained was 155 mg (yield of 8%, starting from daunorubicin) with a m.p=155–157° C. (decomp.). $R_f=0.31$ in chloroform-methanol-water-formic acid (13:6:1:0.05).

Example 3

Antitumor Effect of Galactomycin I and Galactomycin II compared with that of Adriamycin

The response of subcutaneously implanted lymphocyte leukemia P-388 (Arthur D. Little Inc., Cambridge, Mass.) to treatment with a Galactomycin I, Galactomycin II, and Doxorubicin was evaluated in male BDF1 mice.

Mice were acclimated in the laboratory one week prior to experimentation. The animals were housed five per cage in a 12-hour light/dark cycle. The animals received filtered water and sterile rodent food ad libitum. The animals were observed daily and clinical signs were noted. Weight of the animals was in the range of 19–21 g at the day of treatment initiation. The mice were healthy, not previously used in other experimental procedures.

There were a total of twelve groups, 10 animals in two control groups (saline only), and six animals in each in 10 agent treatment groups. The groups were treated 24 hours after tumor implantation, as follows:

(1) Saline (NaCl, 0.9%),
(2) Saline (NaCl, 0.9%),
(3) Adriamycin (7 mg/kg),
(4) Adriamycin (14 mg/kg),
(5) Galactomycin I (7 mg/kg),
(6) Galactomycin I (14 mg/kg),
(7) Galactomycin I (20 mg/kg),
(8) Galactomycin I (40 mg/kg),
(9) Galactomycin II (7 mg/kg),
(10) Galactomycin II (14 mg/kg),
(11) Galactomycin II (40 mg/kg),
(12) Galactomycin II (80 mg/kg).

Tumor cells were implanted in a sub-cutaneous injection of one million cells per mouse and allowed to grow for 24 hours. After that, Adriamycin, Galactomycin I and Galactomycin II were administered as 0.7–10 mg/mL solutions by a single i.v. injection.

Study duration was twenty days after tumor implantation, or nineteen days after treatment initiation. Nonspecific (toxic) deaths and mean survival time, recorded in each group is shown in Table 1 below.

Both Galactomycin I and Galactomycin II are significantly less toxic compared to Adriamycin. A dose of 14 mg/kg of Adriamycin resulted in two nonspecific (toxic) deaths out of six animals, and two animals lived longer than the duration of the study (20 days). However, doses as high as 40 mg/kg (for Galactomycin I) and 80 mg/kg (for Galactomycin II) resulted in only one nonspecific death each, and in each of these cases two animals also lived longer than 20 days.

Weight loss of animals also shows that both Galactomycins I and II are less toxic compared to Adriamycin. In all the three groups, described above (Adriamycin 14 mg/kg, Galactomycin I 40 mg/kg, and Galactomycin II 80 mg/kg), when two animals in each group lived longer than the duration of the study, an average weight loss of an animal was 1.8 g (Adriamycin), 0.9 g (Galactomycin I) and 1.0 g (Galactomycin II). That is, practically the same result in terms of survival time was reached with less side effects with Galactomycin I and II compared with Adriamycin.

TABLE 1

| Animal group | | Nonspecific deaths per group | Average weight gain/loss from day 1 to day 7 (g) | Average survival time, days | |
|---|---|---|---|---|---|
| | | | | Including nonspecific deaths | Excluding nonspecific deaths |
| Agent | Dose, mg/kg | | | | |
| Control (saline) | — | 0 | +5.2 | 9.7 | 9.7 |
| Control (saline) | — | 0 | +5.2 | 9.1 | 9.1 |
| Adriamycin | 7 | 0 | −0.5 | 15.5 | 15.5 |
| | 14 | 2 | −1.8 | >15 | >19 |
| Galactomycin I | 7 | 0 | +1.7 | 11.7 | 11.7 |
| | 14 | 0 | +2.3 | 12.2 | 12.2 |
| | 20 | 0 | −0.8 | 16.3 | 16.3 |
| | 40 | 1 | −0.9 | >16 | >18 |
| Galactomycin II | 7 | 0 | +4.3 | 11.7 | 11.7 |
| | 14 | 0 | +0.8 | 12.0 | 12.0 |
| | 40 | 0 | −1.1 | 15.0 | 15.0 |
| | 80 | 1 | −1.0 | >16 | >18 |

Example 4

Reduction in Side Effects for Galactomycin I and Galactomycin II compared with that of Adriamycin Male BDF1 mice were used as the experimental animals for measuring side effects of therapeutic preparations. Mice were acclimated in the laboratory one week prior to experimentation. The animals were housed five per cage in a 12-hour light/dark cycle. The animals received filtered water and sterile rodent food ad libitum. The animals were observed daily and clinical signs were noted. Weight of the animals was in the range of 19–21 g at the day of treatment initiation. The mice were healthy, not previously used in other experimental procedures.

A single dose intravenous injection of Adriamycin, Galactomycin I or Galactomycin II was provided via the tail vein at the doses listed in Table 2, and the animals were observed for clinical signs immediately after injection, and daily for the duration of the study (20 days).

There were a total of 18 groups of six animals each, as shown in Table 2.

Animals injected with NaCl alone did not show any signs of side effects and all the animals survived of the study.

Three out of six animals in the Adriamycin (21 mg/kg) group died before the end of the study. This was expected, since $LD_{50}$ for Adriamycin (i.v in mice) is 21.1 mg/kg (The Merck Index, 12th Edition, p. 582).

TABLE 2

| Animal group (six animals each) | | Deaths | Life span after treatment, |
|---|---|---|---|
| Agent | Dose, mg/kg | per group | days (except survived animals) |
| Control (saline) | — | 0 | — |
| Doxorubicin | 21 | 3 | 0, 1, 2 |
| Galactomycin I | 10 | 0 | — |
| | 15 | 0 | — |
| | 20 | 0 | — |
| | 25 | 0 | — |
| | 30 | 0 | — |
| | 40 | 1 | 2 |
| | 80 | 6 | 1, 1, 2, 2, 2, 2 |
| | 100 | 6 | 1, 1, 1, 2, 2, 2 |

TABLE 2-continued

| Animal group (six animals each) | | Deaths | Life span after treatment, |
|---|---|---|---|
| Agent | Dose, mg/kg | per group | days (except survived animals) |
| Galactomycin II | 15 | 0 | — |
| | 20 | 0 | — |
| | 25 | 0 | — |
| | 30 | 0 | — |
| | 40 | 0 | — |
| | 50 | 0 | — |
| | 80 | 1 | 2 |
| | 100 | 3 | 1, 1, 2 |

As were observed in Example 3, both Galactomycin I and Galactomycin II are significantly less toxic compared to Adriamycin. Data described in this Example confirm that the $LD_{50}$ value for Adriamycin for a single injection in mice is close to 21 mg/kg. Estimated values for the $LD_{50}$ for Galactomycin I and Galactomycin II are about 50–60 mg/kg and 100 mg/kg, respectively.

The above data illustrates how a chemical attachment of D-galactose residue to the 3'-amino group of Adriamycin via a linker (4 to 6 carbons in length) reduces side effects associated with Adriamycin 3 to 5 times, without changing efficacy of its therapeutic action for treating a particular form of cancer.

All reference cited herein are incorporated by reference.

What is claimed is:

1. A pharmaceutical compound, comprising: a therapeutic agent, a spacer and a galactose, the spacer being covalently linked to the therapeutic agent at a first site on the spacer and the spacer being covalenly linked via an ether linkage with the galactose at a second site on the spacer wherein the spacer linked to galactose has a formula where $n = \geq 0$ and $\leq 20$, or where $n = \geq 0$ and $\leq 20$ and $m = \geq 0$ and $\leq 50$.

2. A pharmaceutical compound according to claim 1, wherein the spacer is a selected from an aldose and a ketose.

3. A pharmaceutical compound according to claim 1, further comprising the agent linked to $-CH_2-(CHOH)_n-CH_2-O-$(Galactose) where $n = \geq 0$ and $<20$.

4. A pharmaceutical compound according to claim 1, further comprising the agent linked to where $n = \geq 0$ and $<20$ and $m = \geq 0$ and $<20$ 5. A pharmaceutical compound according to claim 3, wherein the spacer is an open chain saccharide selected from a triose, a tetrose, a pentose, a hexose and a septose.

6. A pharmaceutical compound according to claim 1, wherein the first site is separated from the second site by at least two carbon atoms.

7. A pharmaceutical compound according to claim 3, wherein the spacer is an open chain hexose.

8. A pharmaceutical compound according to claim 1, wherein a covalent linkage is formed with a reactive group on the therapeutic agent, the reactive group being selected from an amino group, a alkoxy group, a hydroxy group, a carbonyl group, a carboxylic group, a halogen and a thiol group.

9. A pharmaceutical compound according to claim 1, wherein the therapeutic agent is Adriamycin.

10. A pharmaceutical compound according to claim 9, wherein the spacer is covalently linked to an amine group on the daunosamine.

11. A pharmaceutical compound according to claim 8, wherein the galactose is linked to the spacer by means of a glycosidic linkage.

12. A pharmaceutical compound according to claim 1, further comprising N-[β-D-galactopyranosyl-(1→4)-β-O-D-sorbityl]doxorubicin.

13. A pharmaceutical compound according to claim 1, further comprising N-[α-D-galactopyranosyl -(1→6)-β-O-D-sorbityl]doxorubicin.

14. A pharmaceutical preparation, comprising: an effective dose of a compound according to claim 1 and a pharmaceutically acceptable excipient.

15. A method for synthesizing a pharmaceutical compound, comprising:
   (a) providing (i) a therapeutic agent; and (ii) a spacer linked to galactose;
   (b) protecting reactive groups on the therapeutic agent other than at a reactive site for linking to the spacer;
   (c) reacting the protected therapeutic agent with the spacer linked to galactose; and
   (d) deprotecting the therapeutic agent to form the pharmaceutical compound,
wherein the protecting, reacting and deprotecting steps are performed using protic solvents.

16. A method according to claim 15, wherein the spacer linked to galactose has a formula:

where $n = \geq 0$ and $\leq 20$.

17. A method according to claim 15, wherein the spacer linked to galactose has a formula:

where $n = \geq 0$ and $<20$ and $m = \geq 0$ and $<20$.

18. A method according to claim 15, wherein the spacer is an aldose or ketose.

19. A method according to claim 18, wherein the spacer is a hexose.

20. A method of treating a chronic disease in a subject, comprising:
   administering to a subject, an effective dose of a pharmaceutical compound according to claim 1.

21. A method of treating a subject suffering from a medical condition, so as to reduce side effects associated with a therapeutic agent selected for treating the condition without substantially reducing efficacy of the agent, comprising:
   (a) providing as a conjugate, the therapeutic agent covalently linked to a spacer at a first site and galactose covalently linked to the spacer at a second site, wherein the spacer linked to galactose has a formula where $n = \geq 0$ and $\leq 20$, or where $n = \geq 0$ and $\leq 20$ and $m = \geq 0$ and $\leq 50$; and
   (b) administering an effective dose of the conjugate to the subject so that the side effects in the subject are less then they would have been with the unconjugated therapeutic agent.

22. A method according to claim 21, wherein the medical condition is selected from a proliferative disease, high cholesterol, depression, asthma, hypertension and bacterial infections.

23. A method according to claim 21, wherein the proliferative disease is a tumor.

24. A method according to claim 21, wherein the proliferative disease is lymphocytic leukemia.

25. A method according to claim 21, wherein the therapeutic agent is Adriamycin.

26. A method according to claim 21, wherein the spacer is selected from a ketose and an aldose.

27. A method according to claim 21, wherein the galactose is linked via an ether linkage to the galactose.

28. A method according to claim 21, wherein the spacer is selected from (agent) —CH$_2$—(CHOH)$_n$—CH2—O—(Galactose) where n=≧0 and <20, or (agent)

where n=≧0 and <20 and m=≧0 and <20.

29. A method according to claim 21, wherein the conjugate is selected from N-[β-D-galactopyranosyl-(1→4)-β-O-D-sorbityl]doxorubicin and N-[α-D-galactopyranosyl-(1→6)-β-O-D-sorbityl]doxorubicin.

* * * * *